(12) United States Patent
Jung et al.

(10) Patent No.: US 12,140,546 B2
(45) Date of Patent: Nov. 12, 2024

(54) SURFACE-ENHANCED RAMAN SCATTERING PATCH AND ATTACHABLE SENSOR USING THE SAME

(71) Applicant: KOREA INSTITUTE OF MACHINERY & MATERIALS, Daejeon (KR)

(72) Inventors: Ho-Sang Jung, Changwon-Si (KR); Dong-Ho Kim, Changwon-Si (KR); Sung-Gyu Park, Changwon-Si (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 279 days.

(21) Appl. No.: 17/054,200

(22) PCT Filed: Jul. 4, 2019

(86) PCT No.: PCT/KR2019/008221
§ 371 (c)(1),
(2) Date: Nov. 10, 2020

(87) PCT Pub. No.: WO2020/017797
PCT Pub. Date: Jan. 23, 2020

(65) Prior Publication Data
US 2021/0247319 A1      Aug. 12, 2021

(30) Foreign Application Priority Data
Jul. 16, 2018   (KR) ................ 10-2018-0082278

(51) Int. Cl.
*G01N 21/65*  (2006.01)
*A61B 5/00*  (2006.01)

(52) U.S. Cl.
CPC ........ *G01N 21/658* (2013.01); *A61B 5/6833* (2013.01); *A61B 2562/12* (2013.01); *A61B 2562/16* (2013.01)

(58) Field of Classification Search
CPC ........................ G01N 21/658; A61B 5/6833
See application file for complete search history.

(56) References Cited

U.S. PATENT DOCUMENTS

2006/0073336 A1* 4/2006 Zhang ................. G01N 21/658
                                                            428/407
2009/0263912 A1* 10/2009 Yang ................. G01N 21/6489
                                                            977/762
(Continued)

FOREIGN PATENT DOCUMENTS

KR    2003-0008748    1/2003
KR    2010-0110849    10/2010
(Continued)

OTHER PUBLICATIONS

KIPO, PCT Search Report of PCT/KR2019/008221 dated Oct. 8, 2019.

*Primary Examiner* — Rufus L Phillips
(74) *Attorney, Agent, or Firm* — LEX IP MEISTER, PLLC

(57) ABSTRACT

The present invention relates to a surface-enhanced Raman scattering patch and an attachable sensor using same. More particularly, the present invention relates to a surface-enhanced Raman scattering patch which allows continuous monitoring of drug administration and harmful substance detection to be accurately and easily performed, an attachable sensor using same, and a method for manufacturing same.

17 Claims, 12 Drawing Sheets

(56) References Cited

U.S. PATENT DOCUMENTS

| | | | | |
|---|---|---|---|---|
| 2010/0190661 A1* | 7/2010 | Lee | G01N 21/658 | 506/18 |
| 2011/0165586 A1* | 7/2011 | Kim | G01N 21/658 | 435/7.1 |
| 2012/0238840 A1* | 9/2012 | Hashimoto | A61B 5/0075 | 600/310 |
| 2013/0148194 A1* | 6/2013 | Altug | G01N 21/658 | 977/932 |
| 2014/0154668 A1* | 6/2014 | Chou | G01N 21/6486 | 435/7.1 |
| 2015/0036132 A1* | 2/2015 | Bond | C23C 16/405 | 356/244 |
| 2015/0157261 A1* | 6/2015 | Sakagami | A61B 5/4866 | 600/476 |
| 2015/0335249 A1* | 11/2015 | Feldman | G01N 21/658 | 216/26 |
| 2016/0073938 A1* | 3/2016 | Okumura | A61B 5/14532 | 250/216 |
| 2016/0158724 A1* | 6/2016 | Chang | B81C 1/00468 | 29/458 |
| 2019/0170652 A1* | 6/2019 | Dies | G01N 21/658 | |

FOREIGN PATENT DOCUMENTS

| | | |
|---|---|---|
| KR | 2017-0036968 | 4/2017 |
| KR | 2018-0053026 | 5/2018 |
| KR | 2018-0067177 | 6/2018 |
| WO | 2014/196169 | 12/2014 |

\* cited by examiner

- Detection Possible from the Start

SURFACE-ENHANCED RAMAN SCATTERING PATCH AND ATTACHABLE SENSOR USING THE SAME

CROSS-REFERENCE TO RELATED APPLICATIONS

This application is a National Phase Application of PCT International Application No. PCT/KR2019/008221, which was filed on Jul. 4, 2019, and which claims priority from Korean Patent Application No. 10-2018-0082278 filed on Jul. 16, 2018. The disclosures of the above patent applications are incorporated herein by reference in their entirety.

BACKGROUND

1. Technical Field

The present disclosure relates to a surface-enhanced Raman scattering patch and an attachable sensor using the same. More particularly, the present disclosure relates to a surface-enhanced Raman scattering patch that allows a continuous monitoring of drug use and a detection of harmful substances in an accurate and easy manner, an attachable sensor using the same, and a method for manufacturing the same.

2. Description of the Related Art

Methods for testing whether or not an athlete has administered a prohibited drug or taken narcotics mostly involve hair follicle or urine testing.

Generally, a prohibited drugs or narcotics is excreted in its original form or in metabolite form in the urine of the person to whom the drugs or narcotics was administered or injected, and there is a correlation between the time passed since the administration of the prohibited drugs or narcotics and the amount detected in the urine. As such, the most preferable method of testing for prohibited drugs or narcotics would be to perform such a screening test as soon as a urine sample is taken.

However, in cases where taking urine samples is not a viable option or where duration of time has passed since the administering of the prohibited drugs or narcotics until the taking of the urine sample, it may be difficult to obtain accurate test results.

Also, in some cases, it may be necessary to monitor the administering of prohibited drugs during a period in which athletes must participate in sports matches.

One type of drugs testing method uses a chromatography immunodetection strip. In such a method of detecting a drug by using an immunodetction strip, a tested sample is moved along a membrane by capillarity, and when a substance targeted for detection is found, the drug reacts with drug-antibody coloration particulates to form a complex and engages in a competitive reaction with a drug-protein conjugate bonded to the membrane, whereby the presence of a drug can be detected based on the resulting coloration that may occur at this portion.

Currently, there is a continued demand for attachable sensors, etc., that allow a continuous monitoring of prohibited drugs or narcotics use, provide high accuracy, and are convenient to use.

An example of the related art can be found in Korean Patent Publication No. 10-2003-0008748 (Jan. 29, 2003).

The description of the related art set forth above is provided merely to further the understanding of the background of the present disclosure and is not be regarded as an admission that the foregoing is prior art known to the person having ordinary skill in the art.

SUMMARY OF THE INVENTION

An objective of the present disclosure is to provide a surface-enhanced Raman scattering patch and an attachable sensor using the same that enable a continuous monitoring of prohibited drug or narcotics use.

Another objective of the present disclosure is to provide a surface-enhanced Raman scattering patch and an attachable sensor using the same that are convenient to use and provide high accuracy.

The objectives of the present disclosure are not limited to those mentioned above, and other objectives that have not been mentioned will be clearly understood from the detailed descriptions provided below.

One aspect of the present disclosure provides a surface-enhanced Raman scattering patch that includes: a film configured to allow a penetration of detection-target molecules; a metal-containing nanostructure layer formed on the film; and a protective layer formed on the metal-containing nanostructure layer to prevent an entry of outside substances.

According to one embodiment, the film can be a protein film.

According to one embodiment, the protein film can include one or more type selected from silk, collagen, elastin, keratin, and reflectin.

According to one embodiment, the film can have a thickness of 1 nm~1 μm.

According to one embodiment, the metal-containing nanostructure layer can have a thickness of 1 nm~1 μm.

According to one embodiment, the metal-containing nanostructure layer can be composed of one or more types of nanoparticles and nanowires.

According to one embodiment, the metal-containing nanostructure layer can be composed of nanowires having lengths of 1~30 μm.

According to one embodiment, the metal-containing nanostructure layer can be composed of one or more types of nanoparticles and nanowires having diameters of 5~100 nm.

According to one embodiment, the metal of the metal-containing nanostructure layer can be Ag, Au, Al, Co, Cu, Fe, Li, Ni, Pd, Pt, Rh, Ru or an alloy thereof.

According to one embodiment, an interface layer can be included between the film and the metal-containing nanostructure layer.

According to one embodiment, the protective layer can prevent the penetration of the detection-target molecules.

According to one embodiment, the protective layer can be such that allows the penetration of a Raman laser.

According to one embodiment, the protective layer can include an adhesion surface.

According to one embodiment, an adhesion layer formed on the protective layer can be additionally included, and the protective layer and the adhesion layer can be such that allow the penetration of a Raman laser.

According to one embodiment, the protective layer can be waterproof.

Another aspect of the present disclosure provides an attachable surface-enhanced Raman scattering sensor that includes the surface-enhanced Raman scattering patch disclosed herein.

According to one embodiment, the attachable surface-enhanced Raman scattering sensor can be used attached to an animal, a plant, a food packaging, or a medicine packaging.

Still another aspect of the present disclosure provides a method for manufacturing an attachable surface-enhanced Raman scattering sensor, where the method may include: forming a protein film by coating a protein solution; forming a metal-containing nanostructure layer by coating a metal-containing nanostructure solution over the protein film; and forming a protective layer over the metal-containing nanostructure layer after drying.

According to one embodiment, the protein solution can be coated over a substrate having a hydrophobic surface.

According to one embodiment, forming the metal-containing nanostructure layer can include hardening the protein film after coating the metal-containing nanostructure solution.

According to one embodiment, forming the protective layer can include contacting the metal-containing nanostructure layer onto an adhesive surface of the protective layer to transfer the protein film and the metal-containing nanostructure layer onto the protective layer.

An embodiment of the present disclosure makes it possible to provide continuous monitoring for the use of prohibited drugs or narcotics.

An embodiment of the present disclosure can enable testing for prohibited drug or narcotics use that provides high accuracy and is convenient to use.

An embodiment of the present disclosure makes it possible to readily and accurately check for the presence of toxic substances, contamination, or a break in the airtight seal of a packaging, etc., on animals, plants, food packaging, or medicine packaging (for example on fluid pack surfaces).

DETAILED DESCRIPTION OF THE INVENTION

Figure 1:
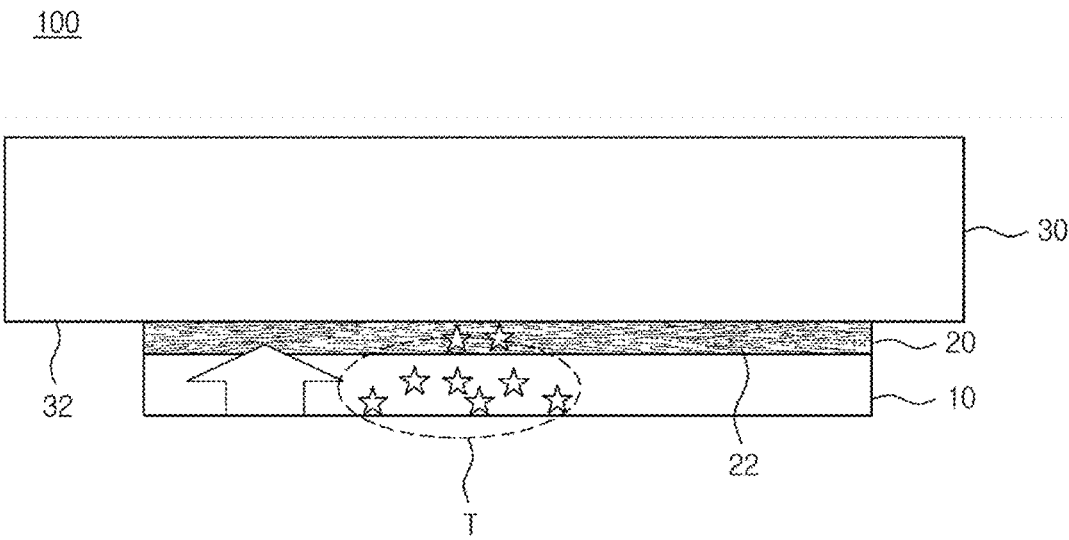
FIG. 1 is a cross-sectional view conceptually illustrating a surface-enhanced Raman scattering patch according to an embodiment of the present disclosure.

The objectives, advantages, and novel features of the present disclosure will be made more clearly apparent from the detailed description and embodiments associated with the appended drawings.

The terms or words used in the present specification are not to be interpreted by their common or dictionary meanings but rather must be interpreted to convey the meanings and concepts that are in accord with the technological spirit of the present disclosure based on the principle that the inventor is permitted to suitably define the concepts of the terms used in the specification in order to best describe the invention.

In the specification, mention of an element such as a layer, part, or substrate being "on", "connected to", or "bonded to" another element can mean that the element is directly "on", "connected to", or "bonded to" the other element but can also mean that one or more other elements are positioned in-between. In contrast, mention of an element being "directly on", "directly connected to", or "directly bonded to" another element means that there are no other elements between the two elements.

The terms used in the present specification are merely used to describe particular embodiments, and are not intended to limit the present disclosure. An expression used in the singular encompasses the expression of the plural, unless it has a clearly different meaning in the context.

In the present specification, it is to be understood that terms such as "including" or "having," etc., are intended to indicate the existence of the features, numbers, steps, actions, elements, parts, or combinations thereof disclosed in the specification and are not intended to preclude the possibility that one or more other features, numbers, steps, actions, elements, parts, or combinations thereof may exist or may be added.

In the specification, mention of a part "including" an element does not preclude the possibility of other elements being present but rather means that one or more other elements can be additionally included, unless specifically stated to the contrary. Also, throughout the specification, the preposition "on" or "over" may refer to a position above or below the object part and does not necessarily refer to an upper position with respect to the direction of gravity.

As the present disclosure allows for various changes and numerous embodiments, particular embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure. In the description of the present disclosure, certain detailed explanations of the related art are omitted when it is deemed that they may unnecessarily obscure the essence of the present disclosure.

Certain embodiments of the present disclosure will be described below in more detail with reference to the accompanying drawings. In describing the appended drawings, identical or corresponding elements are assigned the same reference numeral, and redundant descriptions are omitted.

FIG. 1 is a cross-sectional view conceptually illustrating a surface-enhanced Raman scattering patch according to an embodiment of the present disclosure.

Referring to FIG. 1, a surface-enhanced Raman scattering patch 100 according to an embodiment of the present disclosure may include a film 10 which can be penetrated by detection-target molecules: a metal-containing nanostructure layer 20 formed on the film 10; and a protective layer 30 formed on the metal-containing nanostructure layer 20 to prevent the entry of outside substances.

The film 10 can be any type of film without particular limits as long as the film 10 is capable of absorbing detection-target molecules T, which are released from a test subject such as a human body, etc., and allowing the detection-target molecules T to penetrate to the metal-containing nanostructure layer 20. The detection-target molecules T can include any of solid, liquid, and gaseous states, but in cases where the surface-enhanced Raman scattering patch 100 is used for a drug test, such as when testing for an illegal drug in the human body, the detection-target molecules T can be in an aqueous state. The detection-target molecules T can include, for example, drugs, abused medicines, blood glucose toxic materials, etc.

The film 10 can be a protein film 10. A protein film 10 can easily absorb detection-target molecules T, which may be a drug substance released through sweat or the like in cases where the test subject is a human body, and allow the detection-target molecules T to penetrate to the metal-containing nanostructure layer 20. Also, a protein film 10 is high in biocompatibility, as it is non-toxic to the human body and does not cause immune reactions.

The protein film 10 can include one or more types selected from silk, collagen, elastin, keratin, and reflectin.

The film 10 can have a thickness of 1 nm~1 μm. Although the thickness is not limited thus, a thickness of the film 10 smaller than 1 nm can make it difficult for the film 10 to sufficiently absorb the detection-target molecules T, while a thickness greater than 1 μm can make it difficult for the absorbed detection-target molecules T to reach the metal-containing nanostructure layer 20.

The metal-containing nanostructure layer 20 can be formed on a surface of the film 10 to contain the detection-target molecules T that have arrived after penetrating through the film 10. Multiple metal-containing nanostructures may be present within the metal-containing nanostructure layer 20, and nanogaps between the metal-containing nanostructures may serve as hot spots where plasmon resonance occurs, thereby facilitating the Raman signals enhancement under irradiation.

The metal-containing nanostructure layer 20 can be composed of one or more types of nanoparticles and nanowires 22. The nanoparticles can be of various shapes such as spheres, triangles, stars, rods, tubes, etc., with no particular limits on the shapes of the nanoparticles.

The metal-containing nanostructure layer 20 can be composed of nanowires 22 having lengths of 1~30 μm. The nanowires 22 may be stacked in irregular directions to form multiple cross points. As nanogaps are formed near the cross points and act as hot spots that generate plasmon resonance, thereby greatly facilitating the Raman signals enhancement during irradiation, it can be desirable to form the metal-containing nanostructure layer 20 with nanowires 22. Moreover, since metal-containing nanowires 22 do not have a certain directionality but rather have irregular directions, there is the advantage that the results of analyses using Raman signals are largely independent of the direction of the laser.

The hot spots can be formed vertically and can be formed horizontally. While increasing the thickness to which the metal-containing nanowires 22 are stacked can enhance the Raman signals, the effect of the Raman signals enhancement can become negligible beyond a particular thickness.

The metal-containing nanostructure layer 20 can have a thickness of 1 nm~1 μm. Although the thickness is not limited thus, a thickness of the metal-containing nanostructure layer 20 smaller than 1 nm can make it difficult for the metal-containing nanostructure layer 20 to sufficiently absorb the detection-target molecules T, while a thickness greater than 1 μm would no longer yield a meaningful increase in the Raman signals enhancement with increased thickness.

The metal-containing nanostructure layer 20 can be composed of one or more types of nanoparticles and nanaowires having diameters of 5~100 nm. Although the diameters are not limited thus, diameters of 5~100 nm for the nanoparticles and nanowires 22 can activate hot spots where plasmon resonance occurs, to facilitate the Raman signals enhancement under irradiation.

The metal of the metal-containing nanostructure layer 20 can include any type of metal exhibiting SERS properties and can include Ag, Au, Al, Co, Cu, Fe, Li, Ni, Pd, Pt, Rh, Ru, or an alloy thereof.

Between the film 10 and the metal-containing nanostructure layer 20, an interface layer (not shown) can be included. In cases where the film 10 and the metal-containing nanostructure layer 20 are to be hardened simultaneously, the surface-enhanced Raman scattering patch 100 can have the interface layer formed between the film 10 and the metal-containing nanostructure layer 20.

The protective layer 30 may be formed on the metal-containing nanostructure layer 20 to prevent outside substances from entering and contaminating the detection-target molecules T that have been absorbed into the metal-containing nanostructure layer 20 when the surface-enhanced Raman scattering patch 100 is attached to a test subject.

The protective layer 30 can be composed to prevent a penetration of the detection-target molecules T over the protective layer 30. Such a composition can allow a concentration of the detection-target molecules T that have been absorbed into the metal-containing nanostructure layer 20 and thus increase detection efficiency.

The protective layer 30 can be composed to allow a penetration of a Raman laser. For detaching the surface-enhanced Raman scattering patch 100 that was attached to a test subject such as a human body, and analyzing detection-target molecules T with a Raman spectroscopy analyzer, it can be desirable that the protective layer 30 be transparent to the extent that a Raman laser may penetrate through.

In the present specification, a Raman laser refers to a laser that generates coherent rays with a spectrum component having a different frequency from that of the irradiated rays, i.e. a Stokes frequency or anti-Stokes frequency, when excitation rays are irradiated onto a substance to create stimulated Raman scattering. The Raman laser in the present specification can include any one of the lasers having various known wavelengths and may refer to, but is not limited to, a laser having a wavelength of 200~900 nm.

The protective layer 30 can be provided with an adhesion surface 32 at the surface adjacent to the metal-containing nanostructure layer 20. With such a composition, the protective layer 30 can be used to easily attach the surface-enhanced Raman scattering patch 100 onto the test subject. Also, in cases where the film 10 and the metal-containing nanostructure layer 20 are formed stacked over a substrate, it is possible to manufacture the surface-enhanced Raman scattering patch 100 by transferring the film 10 and the metal-containing nanostructure layer 20 onto the protective layer 30.

The surface-enhanced Raman scattering patch 100 can further include a separate adhesion layer (not shown) on the protective layer 30. In this case, the protective layer 30 and the adhesion layer can be transparent to the extent that the Raman laser may penetrate through.

The protective layer 30 can have a waterproof quality to prevent the penetration of detection-target molecules T and outside substances that are in a liquid state or dissolved in liquid.

A surface-enhanced Raman scattering patch 100 of the present specification can be used attached to a body part other than the skin (such as a nasal membrane, an eye globe, etc.).

Another aspect of the present disclosure provides an attachable surface-enhanced Raman scattering sensor that includes a surface-enhanced Raman scattering patch disclosed herein.

The attachable surface-enhanced Raman scattering sensor can be attached to an animal, including the human being, a plant, a food packaging, or a medicine packaging for use. Thus, the attachable surface-enhanced Raman scattering sensor can be attached to a human body to detect narcotics, abused drugs, blood glucose levels, etc. Also, the attachable surface-enhanced Raman scattering sensor can be attached to an animal other than the human being, a plant, a food packaging, or a medicine packaging (such as a fluid pack) to test for the presence of toxic substances, contamination, or a break in the airtight seal of the packaging, etc.

While the present specification focuses on surface-enhanced Raman scattering, the present disclosure encompasses cases of measuring detection-target molecules with fluorescence. Also, while the surface-enhanced Raman scattering patch of the present specification can be used for various optical detection applications, it can also be implemented as a component for use as an electrochemical sensor.

Figure 2A:
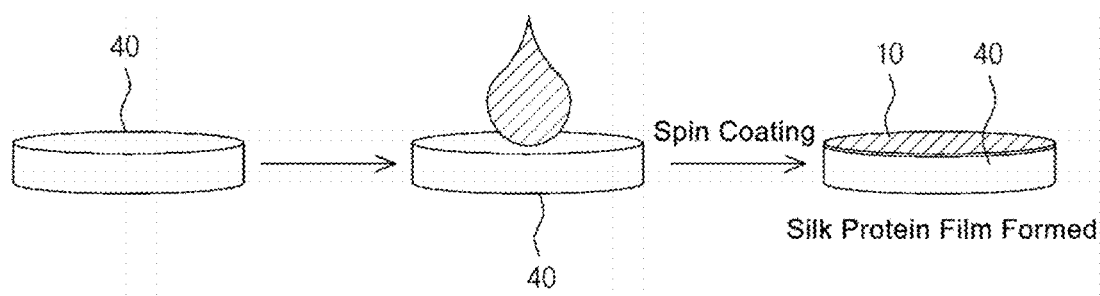
FIG. 2A is a diagram conceptually illustrating a step of forming a protein film in a method for manufacturing a surface-enhanced Raman scattering patch according to an embodiment of the present disclosure.
Figure 2B:
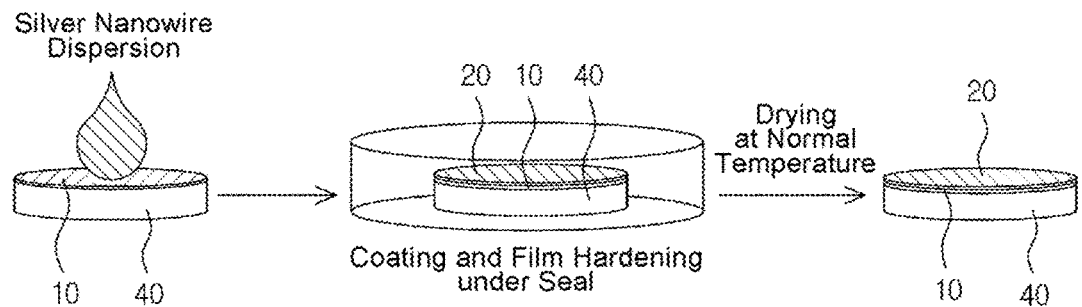
FIG. 2B is a diagram conceptually illustrating a step of forming a metal-containing nanostructure layer in a method for manufacturing a surface-enhanced Raman scattering patch according to an embodiment of the present disclosure.
Figure 2C:
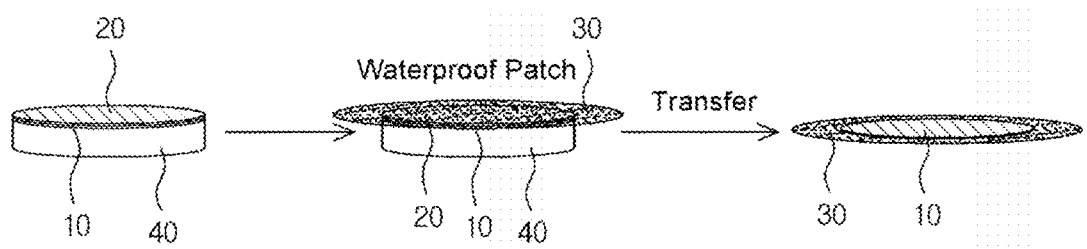
FIG. 2C is a diagram conceptually illustrating a step of forming a protective layer in a method for manufacturing a surface-enhanced Raman scattering patch according to an embodiment of the present disclosure.

FIGS. 2A to 2C are diagrams conceptually illustrating a method for manufacturing a surface-enhanced Raman scattering patch according to an embodiment of the present disclosure.

A method for manufacturing an attachable surface-enhanced Raman scattering patch may include: forming a protein film 10 by coating a protein solution; forming a metal-containing nanostructure layer 20 by coating a metal-containing nanostructure solution over the protein film 10; and forming a protective layer 30 over the metal-containing nanostructure layer 20 after drying.

Referring to FIG. 2A, forming the protein film 10 can include placing and coating a protein solution over a substrate 40 to form the protein film 10.

The substrate 40 can be a substrate having a hydrophobic surface. Such a composition allows an easier transfer when the protein film 10 and the metal-containing nanostructure layer 20 are transferred onto the protective layer 30 for the manufacturing of the attachable surface-enhanced Raman scattering patch.

The protein film 10 can be formed by any of a variety of coating methods such as spin coating, spray coating, bar coating, etc. Although the method is not limited thus, using a spin coating method can enable a quick and uniform coating.

Although the type is not limited thus, the substrate 40 can be a polystyrene film or dish. In an embodiment of the present disclosure, a Petri dish lid having a hydrophobic quality and made of polystyrene was used as the substrate 40, and the protein film 10 was formed with spin coating.

The operation of forming the protein film 10 can include coating a protein solution over the substrate 40 and subsequently hardening the protein solution. With such a composition, the metal-containing nanostructure layer 20 can be easily coated over the protein film 10.

To allow a sufficient absorption of detection-target molecules T, it can be desirable to form the protein film 10 by coating a protein solution in an amount of 35 µL/cm$^2$ or more.

Also, to allow a sufficient absorption of detection-target molecules T, it can be desirable to form the protein film 10 from a protein solution having a concentration of 1~40 weight %.

The protein film 10 can be formed in a thickness of 1 nm~1 µm. Although the thickness is not limited thus, a thickness of the film 10 smaller than 1 nm can make it difficult for the film 10 to sufficiently absorb the detection-target molecules T, while a thickness greater than 1 µm can make it difficult for the absorbed detection-target molecules T to reach the metal-containing nanostructure layer 20.

Referring to FIG. 2B, the operation of forming the metal-containing nanostructure layer 20 can include placing and coating a metal-containing nanostructure dispersion over the protein film 10.

The metal-containing nanostructure dispersion can be prepared by dispersing metal-containing nanostructures in an organic solvent. Here, the organic solvent may serve to disperse the metal-containing nanostructures and harden the protein film 10.

The organic solvent can be one or more type selected from ethanol, methanol, and isopropyl alcohol. In an embodiment of the present disclosure, the metal-containing nanostructure layer 20 was formed by coating a dispersion that was prepared by dispersing silver nanowires in ethanol.

For coating the metal-containing nanowires 22 (FIG. 1), any of a variety of methods can be applied, such as drop casting, chemical deposition, spray drying, bar coating, spin coating, etc.

The operation of forming the metal-containing nanostructure layer 20 can include forming the metal-containing nanostructure layer 20 by placing and coating the dispersion of metal-containing nanostructures in an organic solvent, after coating the protein film 10 and before hardening, and then applying a sealing. With such a composition, it is possible to harden the protein film 10 at the same time the metal-containing nanostructure layer 20 is coated. Here, the sealing may serve to prevent the organic solvent from vaporizing or drying before the protein film 10 is sufficiently hardened by the organic solvent. By hardening the protein film 10 at the same time that the metal-containing nanostructure layer 20 is coated, an interface layer can be formed between the film 10 and the metal-containing nanostructure layer 20, allowing Raman signals enhancement.

The protein film 10 may require an hour or longer of hardening, and in cases where an ethanol dispersion is used, a sealing or the like may have to be applied to prevent the ethanol from evaporating and thus maintaining the hour-long hardening. As such, it can be desirable that the hardening be performed while in a sealed state.

After the hardening of the protein film 10 is concluded, the sealing can be removed and drying can be performed. Although the process is not limited thus, the drying can be performed at normal temperature.

The sizes and density of the metal-containing nanowires 22 (FIG. 1) can be adjusted such that the metal-containing nanowires 22 (FIG. 1) form nanogaps with adjacent metal-containing nanowires 22 (FIG. 1) to induce surface plasmon resonance.

Adjusting the density or thickness in which the metal-containing nanowires 22 (FIG. 1) are stacked can be achieved with various factors, and in an embodiment of the present disclosure, the concentration of metal-containing nanowires 22 (FIG. 1) within the dispersion was used for the adjustment.

The metal-containing nanostructure layer 20 can be formed to a thickness of 1 nm~1 µm. Although the thickness is not limited thus, a thickness of the metal-containing nanostructure layer 20 smaller than 1 nm can make it difficult for the metal-containing nanostructure layer 20 to sufficiently absorb the detection-target molecules T, while a thickness greater than 1 µm would not yield a significant increase in the Raman signals.

In the present specification, the thickness of the metal-containing nanostructure layer 20 can be expressed as the thickness at which the increase in Raman signals is saturated. If the thickness at which there is no longer a significant increase in Raman signals is known, this information can be utilized during the manufacturing process. That is, the thickness at which the increase in Raman signals becomes less significantly observable may be recorded, and the thickness to which the metal-containing nanowires 22 are stacked can be configured based on this information. In this way, analyses using Raman signals can be made less dependent on the focal distance of the laser.

Referring to FIG. 2C, the operation of forming the protective layer 30 can include placing a protective layer 30, which is equipped with an adhesive surface 32 at the surface contacting the metal-containing nanostructure layer 20, in contact with the metal-containing nanostructure layer 20 to thereby transfer the protein film 10 and the metal-containing nanostructure layer 20 onto the protective layer.

Figure 3A:
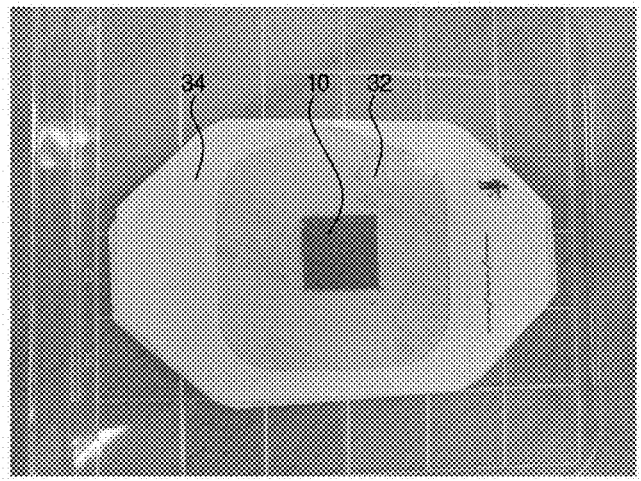
FIG. 3A is a photograph of a surface-enhanced Raman scattering patch according to an embodiment of the present disclosure.
Figure 3B:
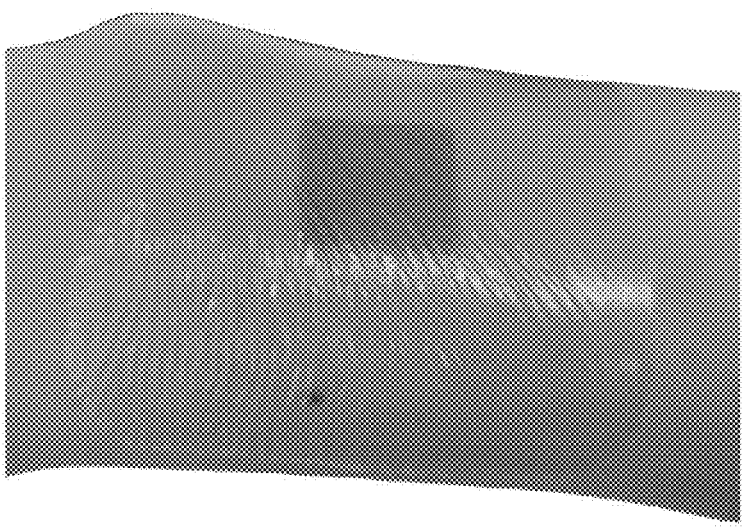
FIG. 3B is a photograph of the surface-enhanced Raman scattering patch of FIG. 3A as attached to the skin.

FIG. 3A is a photograph of a surface-enhanced Raman scattering patch manufactured by a method based on the present disclosure. FIG. 3B is a photograph of the surface-enhanced Raman scattering patch of FIG. 3A as attached to the skin.

Referring to FIG. 3A, a backing sheet 34 can additionally be included, which may cover a portion of the adhesion surface 32 of the protective layer 30. The surface-enhanced Raman scattering patch can be attached to the skin as in FIG. 3B after the backing sheet 34 is removed.

Figure 4A:
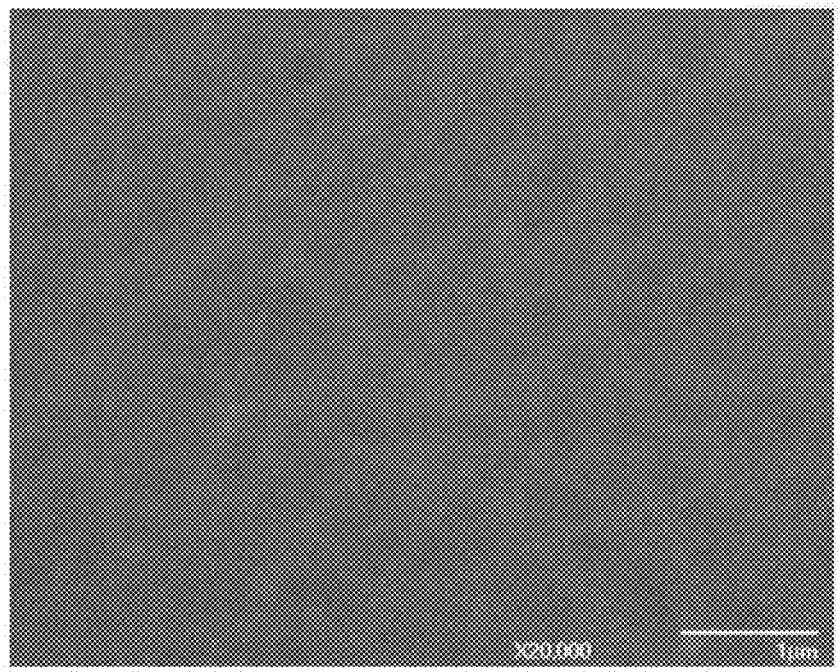
FIG. 4A is a scanning electron microscopy (SEM) image of a film having a nanowire layer formed on one surface according to an embodiment of the present disclosure.
Figure 4B:
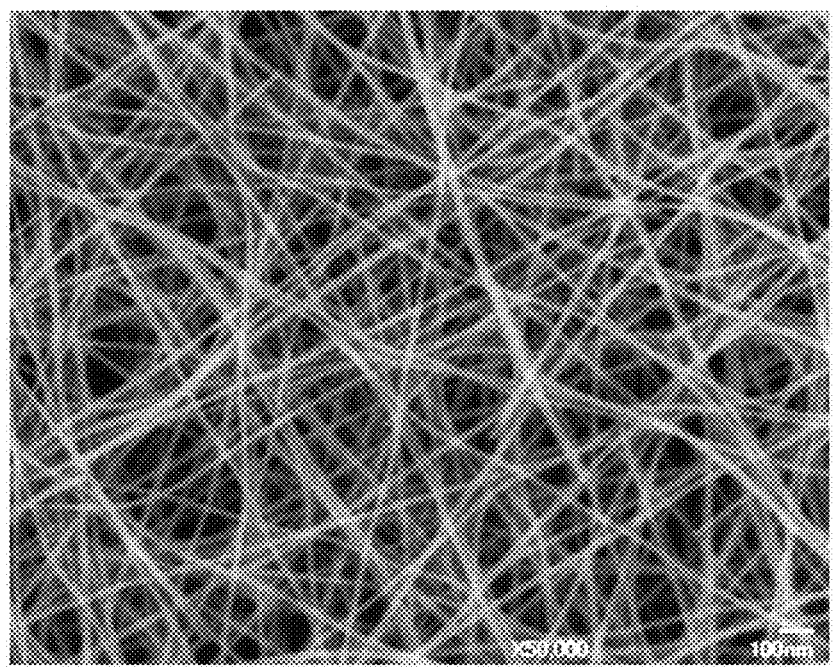
FIG. 4B is a scanning electron microscopy (SEM) image of a nanowire layer formed on a film according to an embodiment of the present disclosure.
Figure 4C:
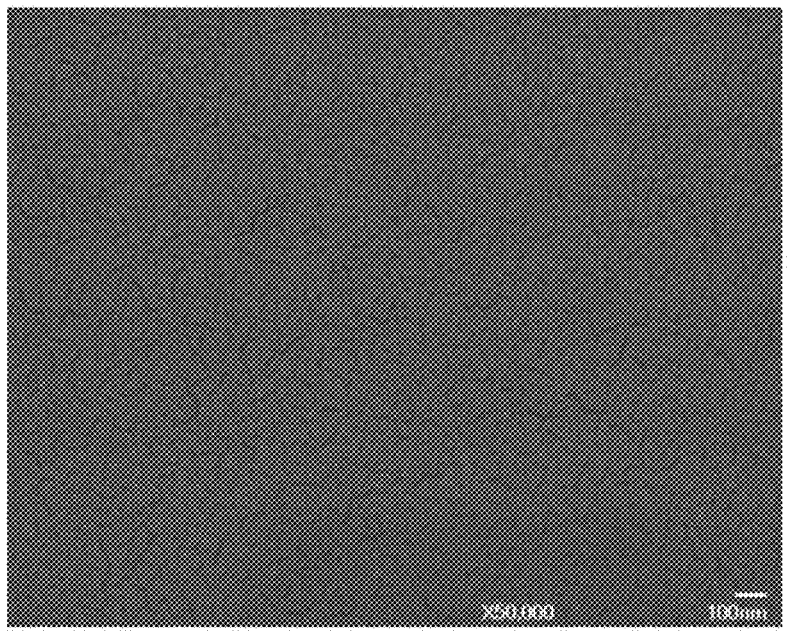
FIG. 4C is a scanning electron microscopy (SEM) image of a surface of the protective layer of a surface-enhanced Raman scattering patch according to an embodiment of the present disclosure.

FIG. 4A is a scanning electron microscopy (SEM) image of a film having a nanowire layer formed on one surface according to an embodiment of the present disclosure. FIG. 4B is a scanning electron microscopy (SEM) image of a nanowire layer formed on a film according to an embodiment of the present disclosure. FIG. 4C is a scanning electron microscopy (SEM) image of a surface of the protective layer of a surface-enhanced Raman scattering patch according to an embodiment of the present disclosure.

The present disclosure is described below in more detail with reference to a case example.

Case Example

1. Forming Silk Protein Films

Silk protein films were formed by spin coating a silk protein (silk fibroin) on a polystyrene dish under the following conditions.

Silk Protein Concentrations: 3 wt % and 6 wt %
Spin Coating Speed: 1000 rpm
Silk Protein Thicknesses: 3 wt %: 60 nm, 6 wt %: 120 nm
Coating Amount: 35 µL/cm$^2$ 2. Forming Metal-Containing Nanostructure Layers Silver nanowire coatings were formed on the spin-coated protein films prepared above as in section 1 under the following conditions.

Coating Material: Silver Nanowires (diameter 20-25 nm, 0.15 wt % ethanol dispersion)
Coating Amount: 35 µL/cm$^2$
Duration of Hardening under Seal: 1 h
Silk protein hardened under a seal in a Petri dish, and silver nanowire interface formed.
Dried at Normal Temperature (No seal)

3. Manufacturing Surface-Enhanced Raman Scattering Patches

The silk protein films on which metal nanostructures were formed were transferred onto 3M Tegaderm™ 1624w films as below.

More specifically, the adhesion surface of a Tegaderm patch was placed in direct contact on each of the silk protein films on which the metal-containing nanostructure layers have been formed, rubbing was applied, and then the Tegaderm patch was detached to transfer the entire film onto the Tegaderm patch (see FIG. 3A).

Figure 5A:
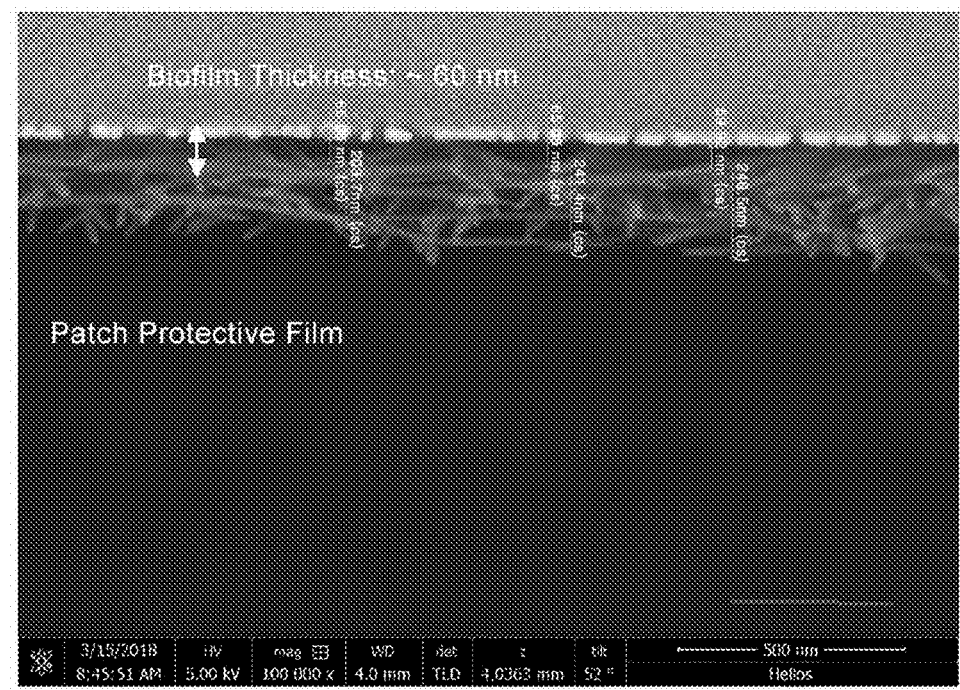
FIG. 5A is a cross-sectional SEM image of a surface-enhanced Raman scattering patch having a film thickness of 60 nm according to an embodiment of the present disclosure.
Figure 5B:
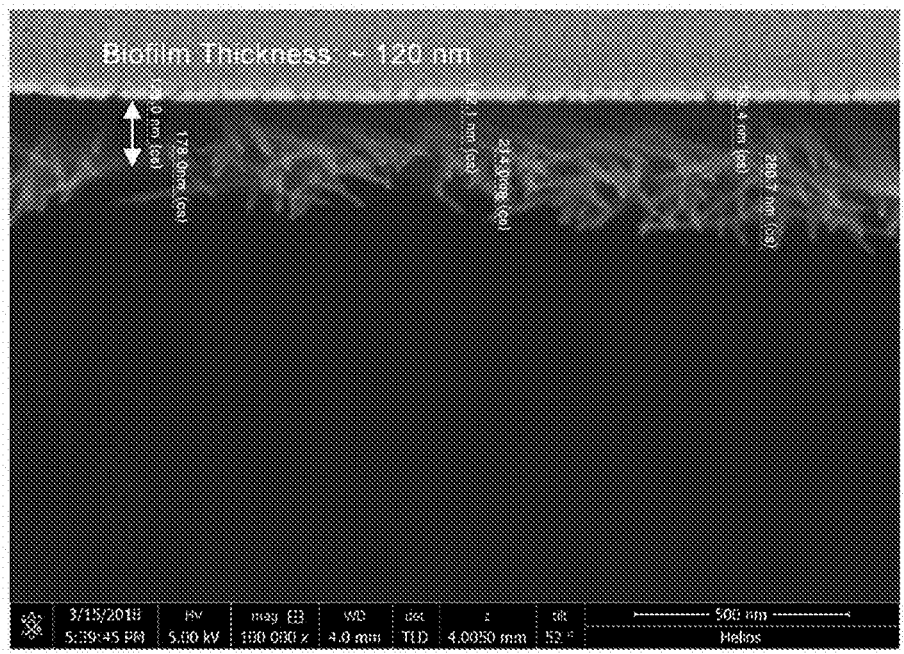
FIG. 5B is a cross-sectional SEM image of a surface-enhanced Raman scattering patch having a film thickness of 120 nm according to an embodiment of the present disclosure.

FIG. 5A is a cross-sectional SEM image of a surface-enhanced Raman scattering patch having a film thickness of 60 nm according to an embodiment of the present disclosure. FIG. 5B is a cross-sectional SEM image of a surface-enhanced Raman scattering patch having a film thickness of 120 nm according to an embodiment of the present disclosure.

Test Example

1. Molecule Penetration Capability of the Silk Protein Film

The silk protein film according to an embodiment of the present disclosure may act as a membrane which, when placed in contact with an aqueous solution containing the detection target molecules, allows molecules of a certain size or smaller to pass through the film and permeate into the metal-containing nanostructure layer but filter out matrix substances and molecules of a particular size or larger.

Figure 6A:
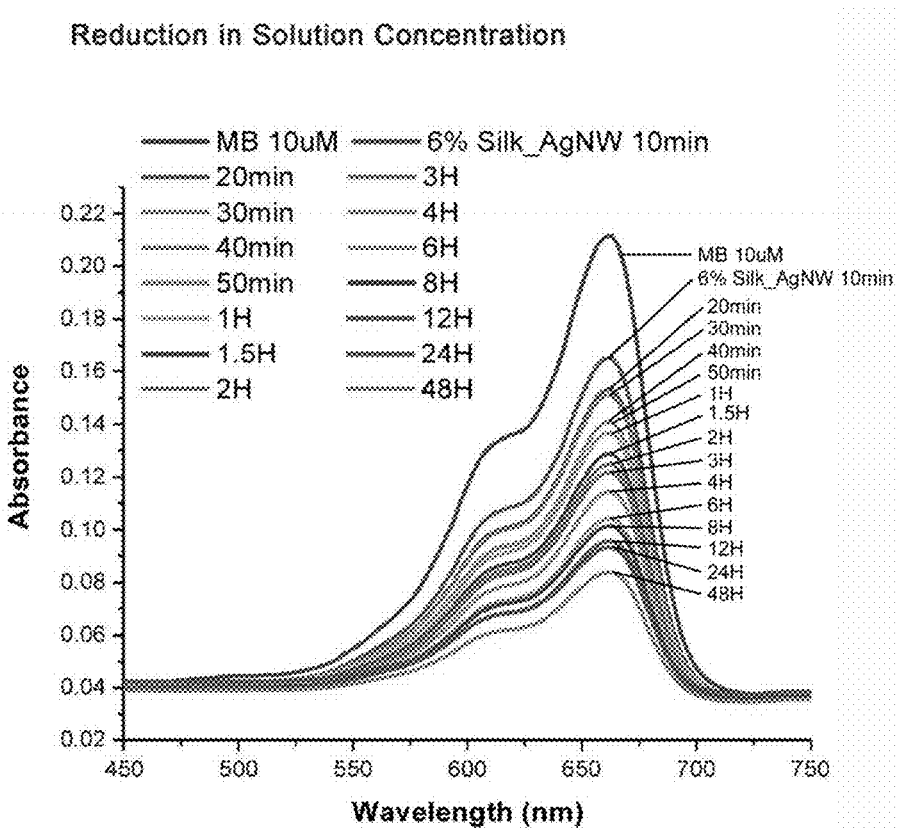
FIG. 6A is a graph representing the results of a methylene blue (MB) penetration test using a surface-enhanced Raman scattering patch according to an embodiment of the present disclosure, with test results shown for different time durations.

FIG. 6A is a graph representing the results of a methylene blue (MB) penetration test using a surface-enhanced Raman scattering patch according to an embodiment of the present disclosure, with test results shown for different time durations. The penetration test was performed using an aqueous solution of 10 µM methylene blue (MB), the example target molecules, with a surface-enhanced Raman scattering patch fabricated from a silk protein of a 120 nm thickness. FIG. 6A shows the results of an example in which a surface-enhanced Raman scattering patch was placed in a MB solution of 10 µM and the supernatant absorbance was measured at different times to measure changes in the MB concentration of the MB solution. The decrease in absorbance of the MB in the solution according to time means that the MB is being absorbed into the surface-enhanced Raman scattering patch.

In order to verify the molecule penetration capability of the silk protein, changes in absorbance were measured for a 10 µM MB aqueous solution using a Tegaderm patch with an exposed adhesion surface, a surface-enhanced Raman scattering patch with the metal-containing nanostructure layer excluded, and a Tegaderm patch having an unexposed adhesion surface, as the control group.

Figure 6B:
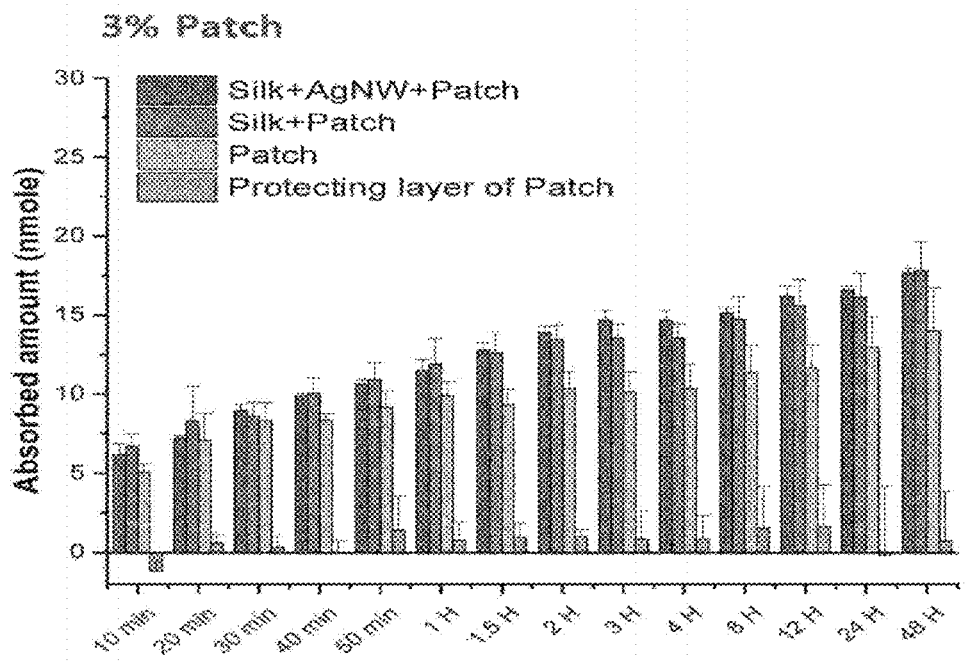
FIG. 6B is a graph representing the results of a methylene blue (MB) penetration test conducted on a surface-enhanced Raman scattering patch manufactured using a 3% concentration of silk protein.
Figure 6C:
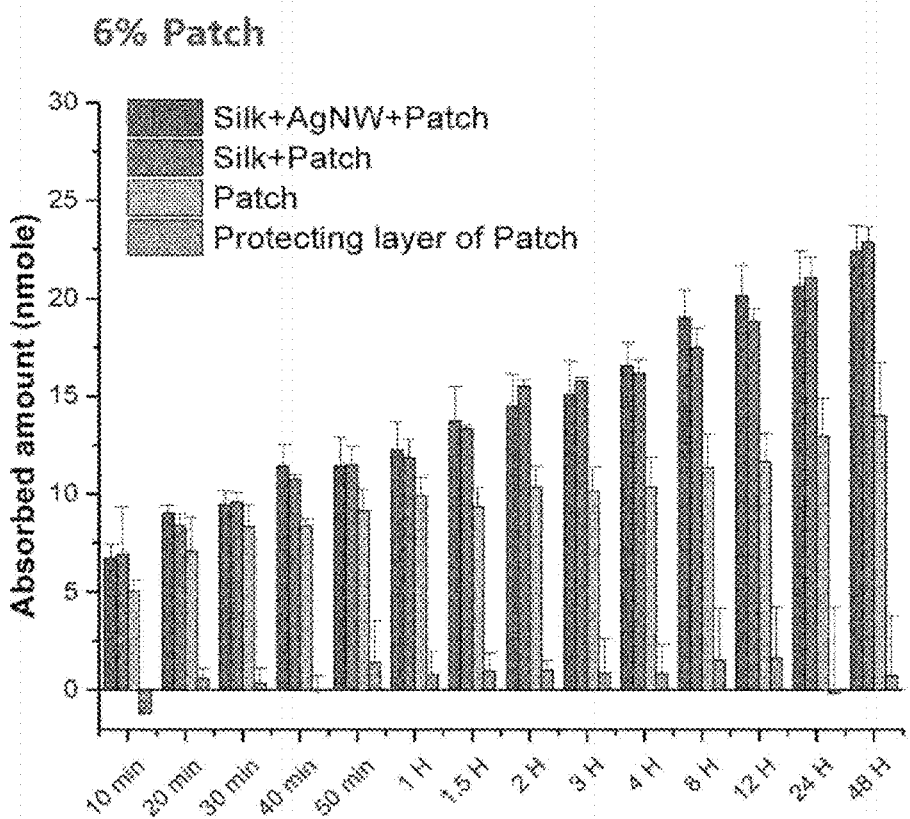
FIG. 6C is a graph representing the results of a methylene blue (MB) penetration test conducted on a surface-enhanced Raman scattering patch manufactured using a 6% concentration of silk protein.

FIG. 6B is a graph representing the results of a methylene blue (MB) penetration test conducted on a surface-enhanced Raman scattering patch manufactured using a 3% concentration of silk protein. FIG. 6C is a graph representing the results of a methylene blue (MB) penetration test conducted on a surface-enhanced Raman scattering patch manufactured using a 6% concentration of silk protein.

FIGS. 6B and 6C are graphs in which the changes in absorbance of each sample are converted to and illustrated as MB amounts. The conversion was performed by obtaining the absorbance Standard curve for each MB concentration and calculating the difference in penetrated amount from the initial concentration in moles.

In FIGS. 6B and 6C, Silk+AgNW+Patch represents the surface-enhanced Raman scattering patch, Silk+Patch represents a patch obtained by excluding the metal nanostructures from the surface-enhanced Raman scattering patch, Patch represents the Tegaderm patch having an exposed adhesion surface, and Protecting layer of Patch represents the Tegaderm patch having an unexposed adhesion surface. From a statistical perspective, Silk+AgNW+Patch and Silk+Patch show no difference in MB molecule penetration capability, which means that the penetration of MB molecules is determined by the silk protein film. With the Tegaderm patch having an exposed adhesion surface, it is determined that a portion of the MB molecules were adhered due to the adhesion surface. With the Tegaderm patch having an unexposed adhesion surface, it can be seen that the MB molecules were not absorbed. Since the adhesion surface of a patch is not exposed due to the silk protein film in an actual surface-enhanced Raman scattering patch, it can be seen that the molecules in the aqueous solution can penetrate through the silk film into the surface-enhanced Raman scattering patch. Moreover, it can be seen that the amount of penetration increases with time.

2. Molecule Detection Capability of the Surface-Enhanced Raman Scattering Patch

FIGS. 7A to 7D are diagrams that conceptually illustrate a method of detecting methylene blue (MB) using a surface-enhanced Raman scattering patch according to an embodiment of the present disclosure.

Figure 7A:
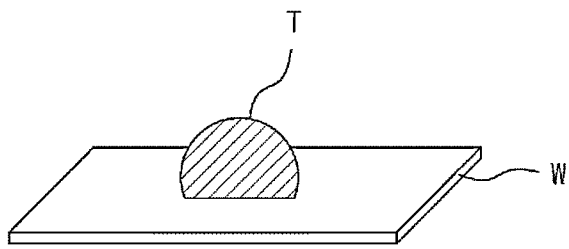
FIG. 7A is a diagram conceptually illustrating a step of loading methylene blue on a silicon wafer in a method of detecting methylene blue (MB) using a surface-enhanced Raman scattering patch according to an embodiment of the present disclosure.
Figure 7B:
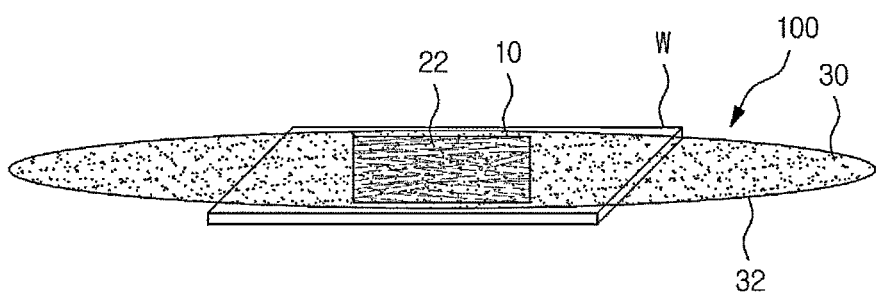
FIG. 7B is a diagram conceptually illustrating a step of placing the silk protein film part of the surface-enhanced Raman scattering patch to cover the loaded solution in a method of detecting methylene blue (MB) using a surface-enhanced Raman scattering patch according to an embodiment of the present disclosure.
Figure 7C:
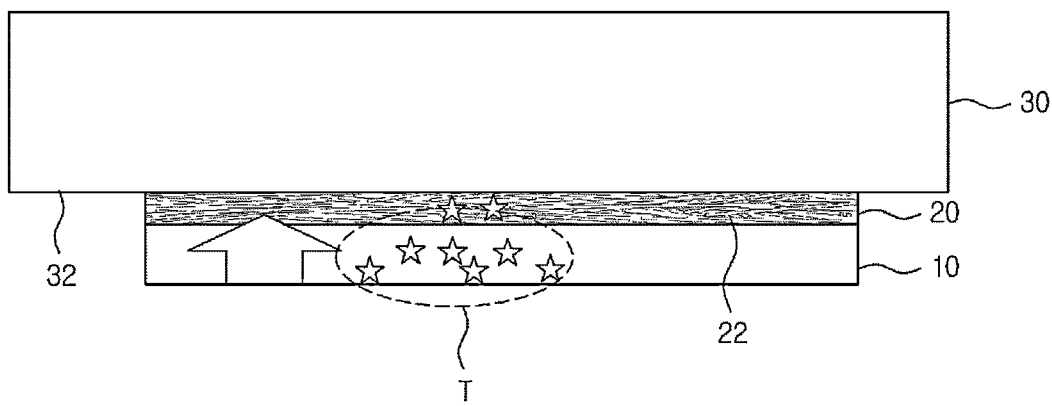
FIG. 7C is a diagram conceptually illustrating a step of inducing the methylene blue to penetrate into the metal-containing nanostructure layer of the surface-enhanced Raman scattering patch in a method of detecting methylene blue (MB) using a surface-enhanced Raman scattering patch according to an embodiment of the present disclosure.

Referring to FIGS. 7A to 7D, in order to check the molecule detection capability of the surface-enhanced Raman scattering patch, 5 µL of methylene blue, which serves as the detection-target molecules T, was loaded on a silicon wafer W (FIG. 7A). The silk protein film 10 portion of the surface-enhanced Raman scattering patch 100 was placed over the loaded solution (FIG. 7B) to induce a penetration of the detection-target molecules to the nanowires 22 of the metal-containing nanostructure layer 20 (FIG. 7C).

Figure 7D:
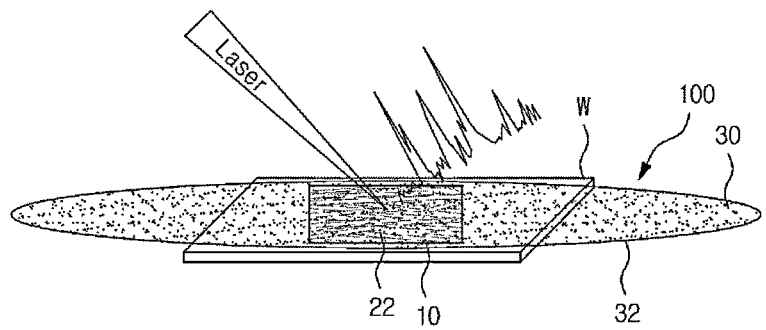
FIG. 7D is a diagram conceptually illustrating a step of irradiating a Raman laser onto the surface-enhanced Raman scattering patch to measure Raman signals in a method of detecting methylene blue (MB) using a surface-enhanced Raman scattering patch according to an embodiment of the present disclosure.

Afterwards, with the exception of the example for measuring signals according to time, the loaded solution was completely dried for a minimum of 4 hours or longer in all cases, and afterwards, a Raman laser was irradiated to measure Raman signals (FIG. 7D). The conditions for measuring the Raman signals were fixed to 5 mW and an exposure time of 0.5 seconds unless specifically mentioned otherwise.

1) LOD

The limits of detection of the MB molecules were measured, using surface-enhanced Raman scattering patches formed on 3% and 6% silk protein.

Figure 8A:
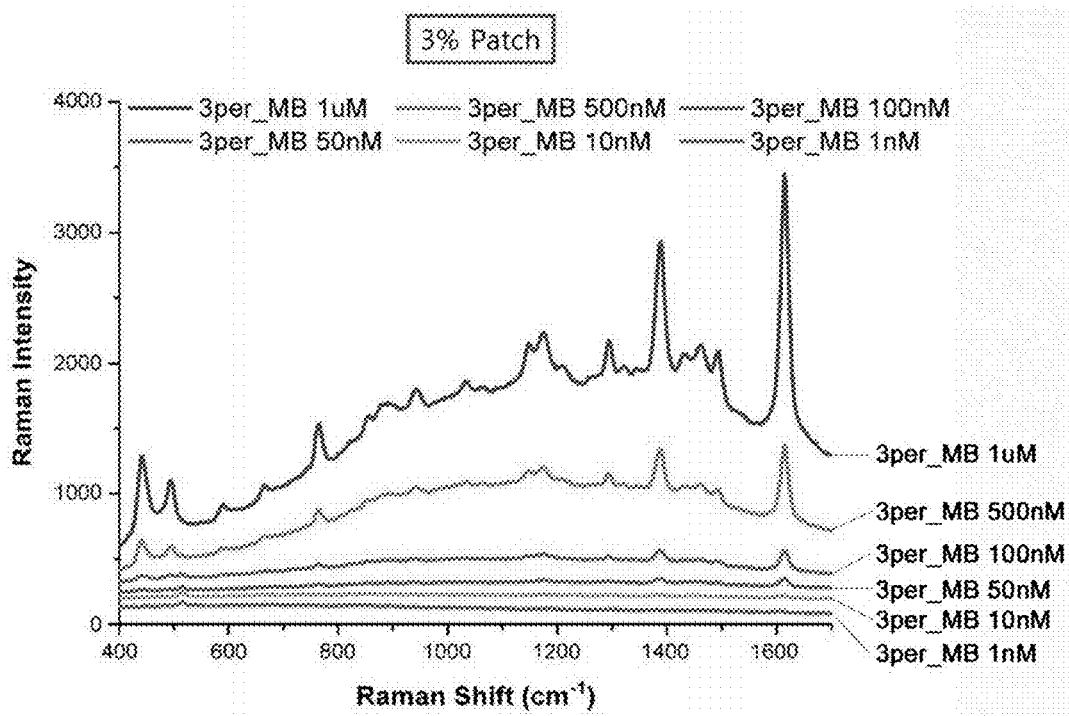
FIG. 8A is a Raman signal graph for different methylene blue (MB) concentrations as measured with a surface-enhanced Raman scattering patch manufactured using a 3% concentration of a silk protein.
Figure 8B:
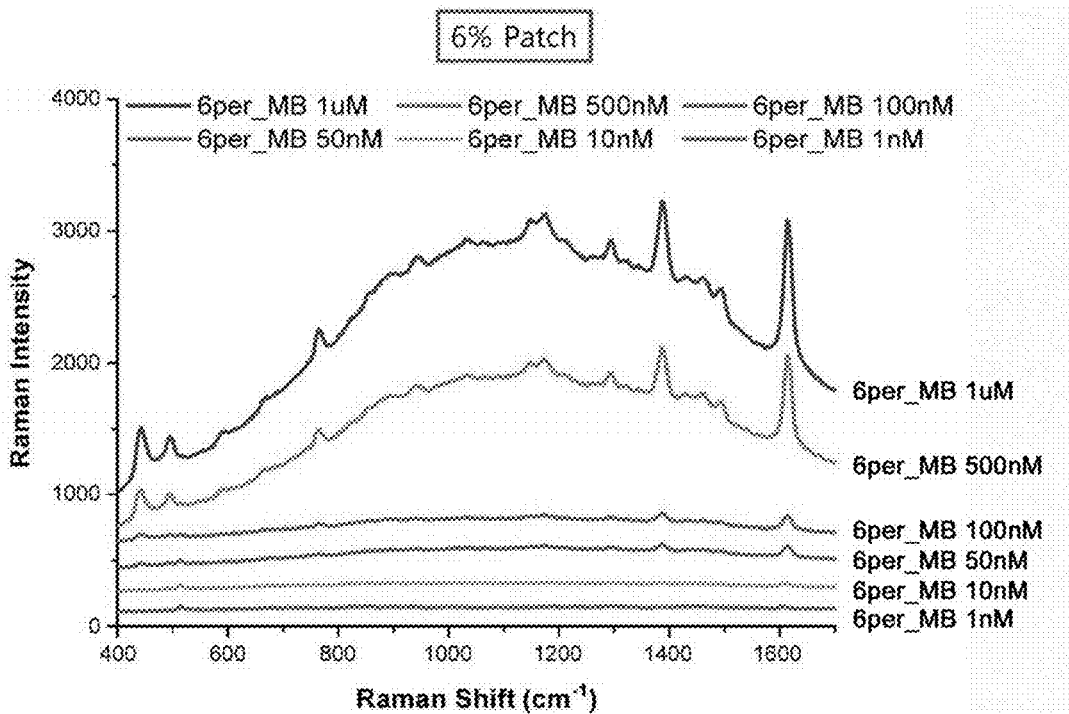
FIG. 8B is a Raman signal graph for different methylene blue (MB) concentrations as measured with a surface-enhanced Raman scattering patch manufactured using a 6% concentration of a silk protein.

FIG. 8A is a Raman signal graph for different methylene blue (MB) concentrations as measured with a surface-enhanced Raman scattering patch manufactured using a 3% concentration of a silk protein. FIG. 8B is a Raman signal graph for different methylene blue (MB) concentrations as measured with a surface-enhanced Raman scattering patch manufactured using a 6% concentration of a silk protein.

Aqueous solutions of MB were prepared with concentrations of 1 μM, 500 nM, 100 nM, 50 nM, and 10 nM, and measurements were taken 24 hours after loading 10 μL of each solution. In each case, the detection limit was 10 nM, and considering the loading amount of 10 μL, this corresponds to 32 μg of MB that can be detected.

2) Cases where Detection-Target Molecules are Accumulated

It was observed whether or not Raman signals would increase when the solution was successively loaded and dried over several repetitions. This was to see whether or not detection is possible if additional detection-target molecules are penetrated after the aqueous solution as penetrated through the silk protein film. A 100 μM MB solution was loaded 10 μL each time and dried for 12 hours, and Raman measurements were taken for four repetitions.

Figure 9:
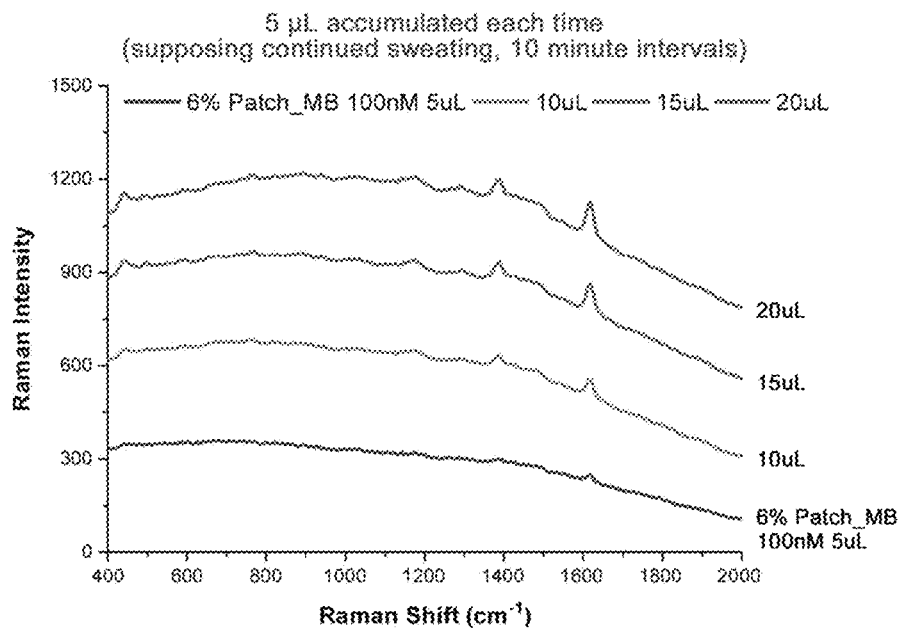
FIG. 9 is a graph representing the results of detecting detection-target molecules accumulated in a surface-enhanced Raman scattering patch according to an embodiment of the present disclosure.

FIG. 9 is a graph representing the results of detecting detection-target molecules accumulated in a surface-enhanced Raman scattering patch according to an embodiment of the present disclosure. From FIG. 9, it can be seen that the Raman signals continue to increase throughout the four repetitions of having the 100 μM MB solution penetrate through the silk protein film. This shows that when the surface-enhanced Raman scattering patch is used for an extended period, it is possible to detect the signals of the accumulated detection-target molecules.

3) Comparison of Substance Penetration Capabilities of Silk Protein for Different Molecular Weights The substance penetration capabilities of silk protein for different molecular weights were compared.

Raman signals were measured for different time durations after loading aminobenzoic acid (ABA), which has a molecular weight of 137, methylene blue (MB), which has a molecular weight of 319, and Rhodamine B (Rho B), which has a molecular weight of 479, in concentrations of 1 mM, 10 μM, and 10 μM, respectively, in a volume of 10 μL each. Measurements were taken at 1 minute, 10 minutes, 20 minutes, 30 minutes, 40 minutes, 50 minutes, 1 hour, 1 hour and 30 minutes, 2 hours, 3 hours, 4 hours, and 24 hours.

Figure 10A:
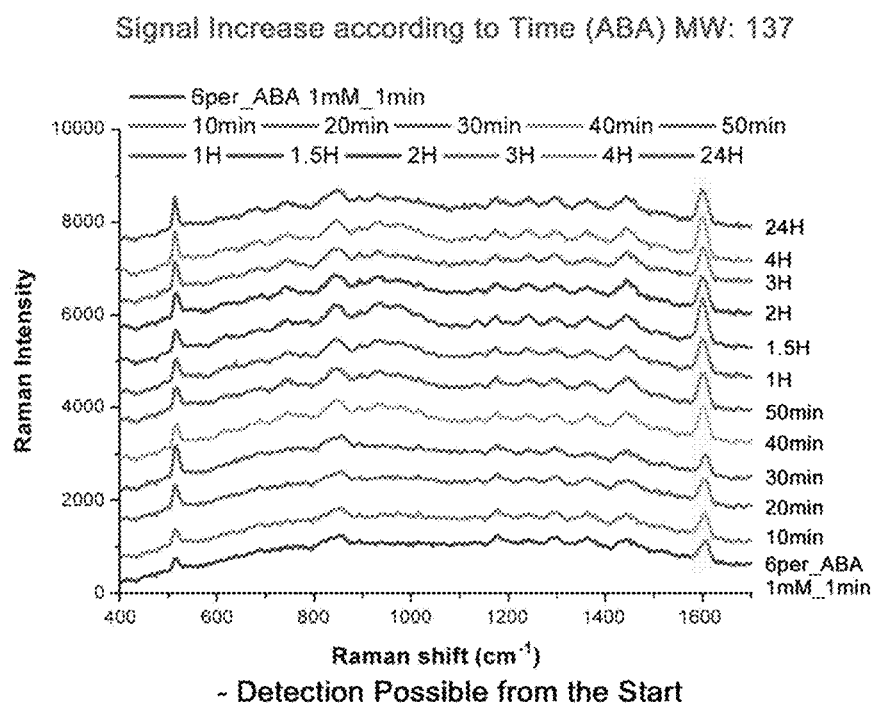
FIG. 10A is a Raman signal graph for different time durations testing the ability of aminobenzoic acid (ABA) to penetrate silk proteins as observed using a surface-enhanced Raman scattering patch according to an embodiment of the present disclosure.
Figure 10B:
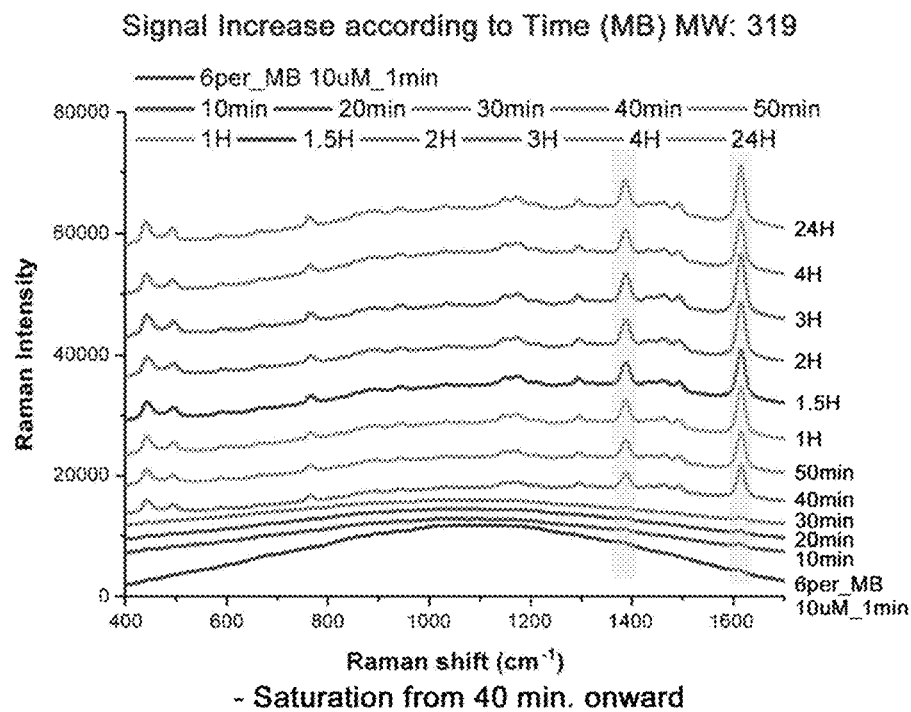
FIG. 10B is a Raman signal graph for different time durations testing the ability of methylene blue (MB) to penetrate silk proteins as observed using a surface-enhanced Raman scattering patch according to an embodiment of the present disclosure.
Figure 10C:
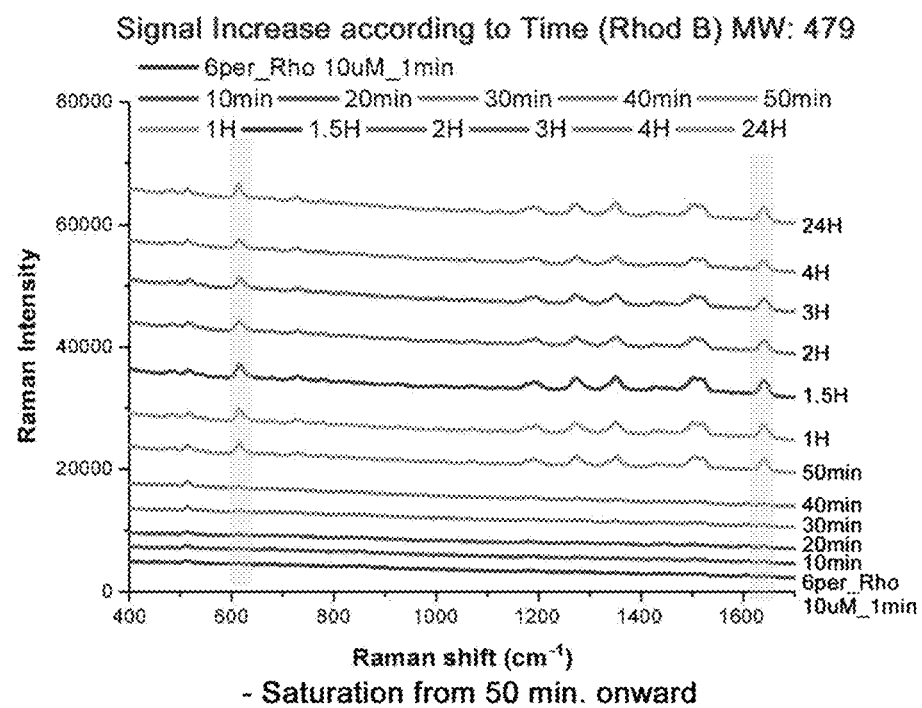
FIG. 10C is a Raman signal graph for different time durations testing the ability of Rhodamine B (Rho B) to penetrate silk proteins as observed using a surface-enhanced Raman scattering patch according to an embodiment of the present disclosure.

FIG. 10A is a Raman signal graph for different time durations testing the ability of aminobenzoic acid (ABA) to penetrate silk proteins as observed using a surface-enhanced Raman scattering patch according to an embodiment of the present disclosure. FIG. 10B is a Raman signal graph for different time durations testing the ability of methylene blue (MB) to penetrate silk proteins as observed using a surface-enhanced Raman scattering patch according to an embodiment of the present disclosure. FIG. 10C is a Raman signal graph for different time durations testing the ability of Rhodamine B (Rho B) to penetrate silk proteins as observed using a surface-enhanced Raman scattering patch according to an embodiment of the present disclosure.

In FIG. 10A, which shows Raman signals of ABA at different time durations, Raman signals ~1380 $cm^{-1}$, 1600 $cm^{-1}$, etc., corresponding to ABA were detected from 1 minute onward. In FIG. 10B, which shows Raman signals of MB at different time durations, Raman signals ~1400 $cm^{-1}$, 1640 $cm^{-1}$, etc., corresponding to MB were detected from 40 minutes onward. In FIG. 10C, which shows Raman signals of Rho B at different time durations, Raman signals ~620 $cm^{-1}$, 1640 $cm^{-1}$, etc., corresponding to Rho B were detected from 50 minutes onward.

From the above results, it can be seen that molecules having smaller molecular weights penetrate through the silk protein film more quickly, while molecules having greater molecular weights penetrate through the film more slowly, resulting in relative time differences in Raman signal detection. While the time point at which Raman signals appear may differ according to the performance of the detection equipment such as the power of the measured laser power, exposure time, etc., the times at which detections occur would be relatively quicker for smaller molecular weights.

4) Raman Signal Reliability of the Surface-Enhanced Raman Scattering Patch

Figure 11A:
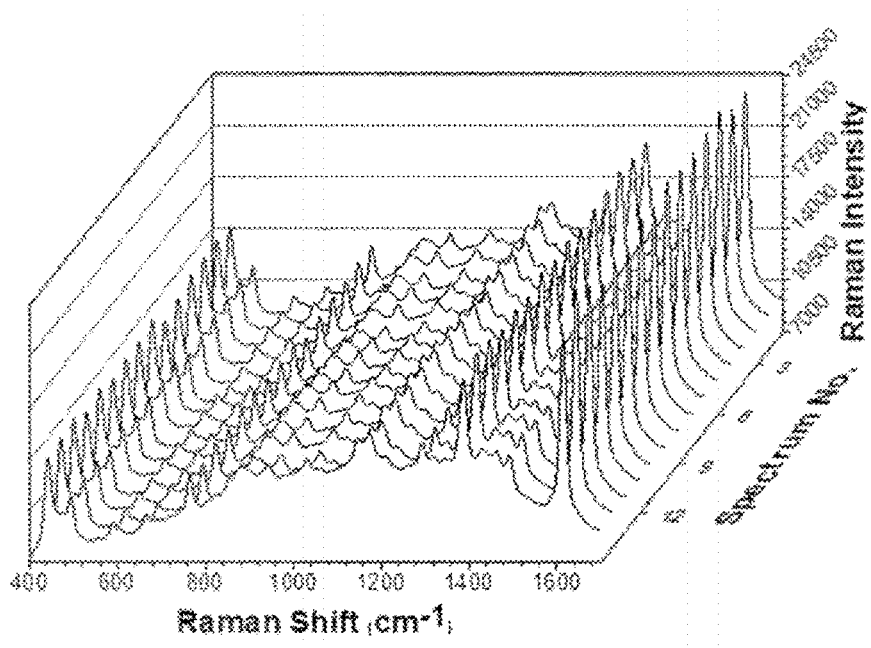
FIG. 11A is a Raman signal graph showing signal uniformity in a surface-enhanced Raman scattering patch according to an embodiment of the present disclosure that has absorbed a 10 μM concentration of methylene blue (MB).

FIG. 11A is a Raman signal graph showing the results of measuring Raman signals at 15 positions on a surface-enhanced Raman scattering patch that has absorbed a 10 μM concentration of MB. As shown in FIG. 11A, the intensities of the Raman signals are measured to be uniform throughout the surface-enhanced Raman scattering patch, from which the Raman signal reliability of the surface-enhanced Raman scattering patch can be confirmed.

Figure 11B:
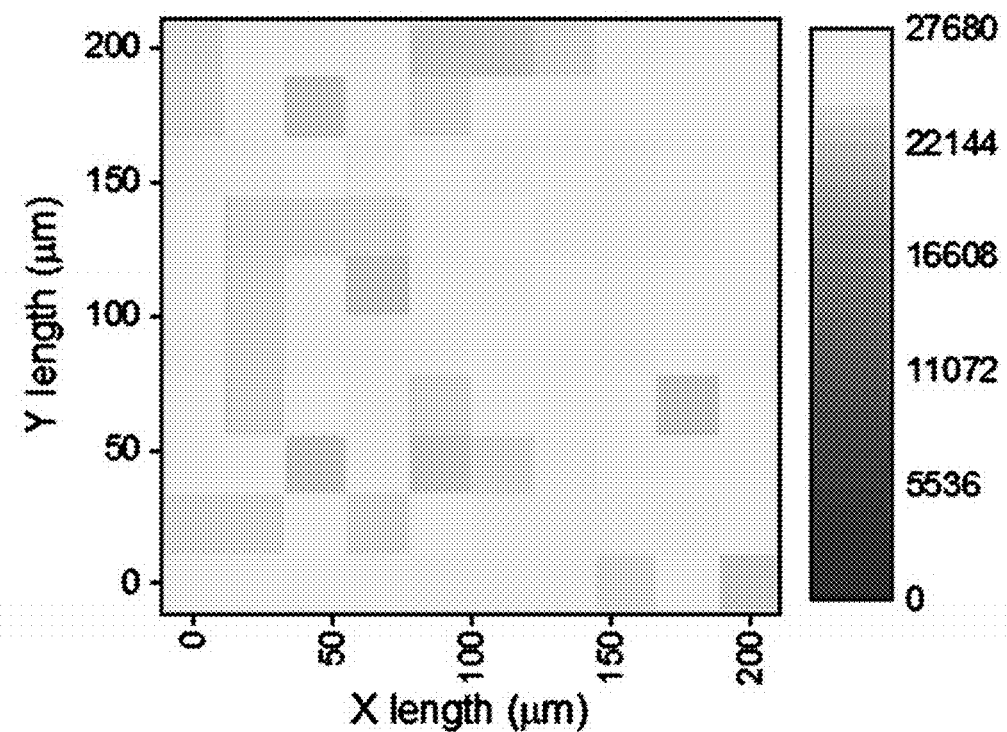
FIG. 11B is a Raman mapping graph in a 0.04 mm² area of a surface-enhanced Raman scattering patch according to an embodiment of the present disclosure that has absorbed a 10 μM concentration of methylene blue (MB).

FIG. 11B is a Raman mapping image showing the results of measuring 100 Raman signals in a 0.04 $mm^2$ area of a surface-enhanced Raman scattering patch that has absorbed a 10 μM concentration of MB, and from FIG. 11B, the high uniformity of Raman signals and reliability of the surface-enhanced Raman scattering patch can be confirmed.

5) Biocompatibility of the Surface-Enhanced Raman Scattering Patch

Figure 12:
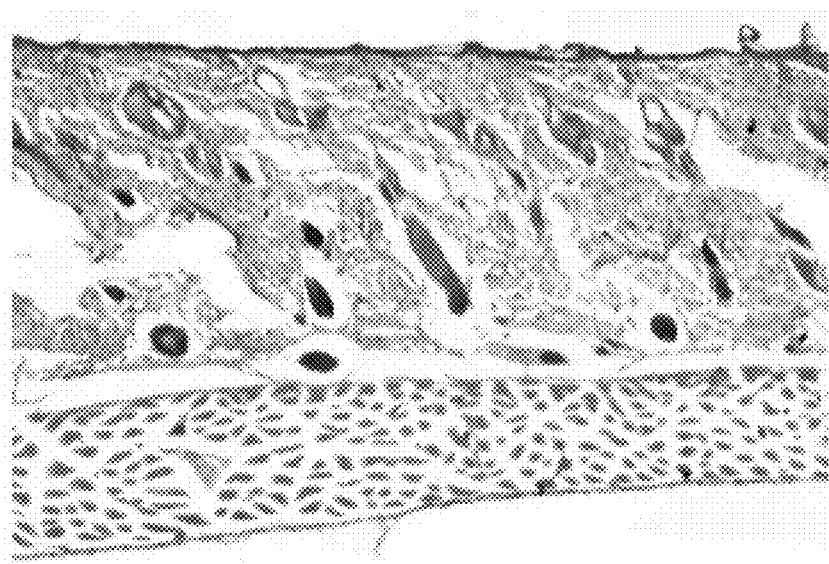
FIG. 12 is a photograph showing the cross section of a rodent skin tissue analyzed after attaching a surface-enhanced Raman scattering patch according to an embodiment of the present disclosure onto the skin of a rodent for 7 days.

FIG. 12 is a photograph showing the results of attaching the surface-enhanced Raman scattering patch onto the skin of a rodent for 7 days, harvesting the cross section of the attached skin, and analyzing the tissue. For the tissue analysis, the harvested tissue was fixed with formalin and dehydrated, paraffin was penetrated to form a block, and a microtome was used to prepare the skin tissue cross section. Afterwards, the paraffin was removed from the skin tissue, and H&E staining was applied, to obtain the tissue photograph of FIG. 12 using an optical microscope.

In the result shown in FIG. 12, there is no penetration of immunocytes observed in the cross section of skin tissue to which the surface-enhanced Raman scattering patch was attached, from which the skin biocompatibility of the developed surface-enhanced Raman scattering patch can be confirmed.

While the foregoing provides a detailed description of the present disclosure by way of specific embodiments, it is apparent that modifications and improvements can be made by the person having ordinary skill in the art without departing from the technical spirit of the present disclosure. Simple modifications and alterations of the present disclosure lie within the scope of the present disclosure, and the specific scope of protection of the present disclosure can be clearly understood from the appended claims.

DESCRIPTION OF REFERENCE NUMERALS

100: surface-enhanced Raman scattering patch
10: film

20: metal-containing nanostructure layer
22: nanowires
30: protective layer
32: adhesion surface
34: backing sheet
40: substrate
T: detection-target molecules
W: wafer

What is claimed is:

1. A surface-enhanced Raman scattering patch configured to be being attached to a test subject comprising:
   a protein film configured to absorb detection-target molecules directly from the test subject, and allow penetration of the detection-target molecules;
   a metal-containing nanostructure coating layer directly disposed on the film such that the absorbed detection-target molecules penetrate to the metal-containing nanostructure layer; and
   a flexible protective layer formed on the metal-containing nanostructure layer, the protective layer configured to prevent an entry of outside substances, and
   an adhesion layer,
   wherein the protein film comprises at least one selected from silk, collagen, elastin, keratin, and reflectin,
   wherein the protective layer and the adhesion layer are transparent to analyze detection-target molecules T with a Raman Spectroscopy analyzer, and
   wherein the metal containing nanostructure layer comprises nanowires and the nanowires are stacked in irregular directions to form multiple cross points.

2. The surface-enhanced Raman scattering patch of claim 1, wherein the film has a thickness of 1 nm~1 μm.

3. The surface-enhanced Raman scattering patch of claim 1, wherein the metal containing nanostructure layer has a thickness of 1 nm~1 μm.

4. The surface-enhanced Raman scattering patch of claim 1, wherein the metal containing nanostructure layer further comprises nanoparticles.

5. The surface-enhanced Raman scattering patch of claim 4, wherein the metal containing nanostructure layer comprises a nanowire having a length of 1~30 μm.

6. The surface-enhanced Raman scattering patch of claim 4, wherein the metal containing nanostructure layer comprises one or more types selected from a group consisting of nanoparticles and nanowires having diameters of 5~100 nm.

7. The surface-enhanced Raman scattering patch of claim 1, wherein the metal containing nanostructure layer comprises a metal selected from a group consisting of Ag, Au, Al, Co, Cu, Fe, Li, Ni, Pd, Pt, Rh, and Ru or an alloy thereof.

8. The surface-enhanced Raman scattering patch of claim 1, wherein the protective layer prevents penetration of the detection-target molecules.

9. The surface-enhanced Raman scattering patch of claim 1, wherein the protective layer allows a penetration of a Raman laser.

10. The surface-enhanced Raman scattering patch of claim 1, wherein the protective layer and the adhesion layer allow a penetration of a Raman laser.

11. The surface-enhanced Raman scattering patch of claim 1, wherein the protective layer is waterproof.

12. An attachable surface-enhanced Raman scattering sensor comprising the surface enhanced Raman scattering patch of claim 1.

13. The attachable surface-enhanced Raman scattering sensor of claim 12, wherein the attachable surface-enhanced Raman scattering sensor is used attached to an animal, a plant, a food packaging, or a medicine packaging.

14. A method for manufacturing an attachable surface-enhanced Raman scattering sensor of claim 12, the method comprising:
   forming a protein film by coating a protein solution;
   forming a metal-containing nanostructure layer by coating a metal-containing nanostructure solution over the protein film; and
   forming a protective layer over the metal-containing nanostructure layer after drying.

15. The method for manufacturing an attachable surface-enhanced Raman scattering sensor according to claim 14, wherein the protein solution is coated over a substrate having a hydrophobic surface.

16. The method for manufacturing an attachable surface-enhanced Raman scattering sensor according to claim 14, wherein the forming of the metal-containing nanostructure layer comprises hardening the protein film after coating the metal-containing nanostructure solution.

17. The method for manufacturing an attachable surface-enhanced Raman scattering sensor according to claim 14, wherein the forming of the protective layer comprises contacting the metal-containing nanostructure layer onto an adhesive surface of the protective layer to transfer the protein film and the metal-containing nanostructure layer onto the protective layer.

* * * * *